United States Patent
Krause

(10) Patent No.: US 6,740,065 B2
(45) Date of Patent: May 25, 2004

(54) EYE DROP CONTAINER TRANSPORT APPARATUS

(76) Inventor: John L. Krause, 7270 Fairfax Dr. No. B-312, Tamarac, FL (US) 33321

( * ) Notice: Subject to any disclaimer, the term of this patent is extended or adjusted under 35 U.S.C. 154(b) by 0 days.

(21) Appl. No.: 09/973,569

(22) Filed: Oct. 9, 2001

(65) Prior Publication Data

US 2003/0028155 A1 Feb. 6, 2003

Related U.S. Application Data

(60) Provisional application No. 60/309,306, filed on Aug. 2, 2001.

(51) Int. Cl.$^7$ .............................................. A61H 33/04
(52) U.S. Cl. ...................................................... 604/302
(58) Field of Search ................................ 604/294–302; 222/420–422

(56) References Cited

U.S. PATENT DOCUMENTS

| | | | | |
|---|---|---|---|---|
| D249 S | * | 11/1849 | Trovinger | D23/346 |
| 3,779,245 A | * | 12/1973 | Windsor | 604/300 |
| 4,531,944 A | * | 7/1985 | Bechtle | 604/302 |
| 5,713,495 A | * | 2/1998 | Menard | 222/212 |
| 6,371,945 B1 | * | 4/2002 | Sherman | 604/300 |
| D463,550 S | * | 9/2002 | Sherman | D24/127 |

* cited by examiner

Primary Examiner—Weilun Lo
Assistant Examiner—Linh Truong

(57) ABSTRACT

An eye drop container transport apparatus that is capable of retaining an eye drop container in a relatively upright manner and assisting users with accurately applying eye drops as well as reducing the incidence of spilled, leaked, or otherwise wasted solution. The eye drop container anchoring apparatus includes a clip portion so that it can be removably secured to an eye drop container and an elongate support arm that extends from the clip portion and helps secure the eye drop container transport apparatus in place. A first and second sight is provided to enable users to increase their proficiency in instilling eyedrops to the eyes while minimizing spillage and wasted solution.

12 Claims, 2 Drawing Sheets

EYE DROP CONTAINER TRANSPORT APPARATUS

CROSS REFERENCE TO RELATED APPLICATION

This application claims the benefit of U.S. Provisional Patent Application Ser. No. 60/309,306 filed Aug. 2, 2001.

BACKGROUND OF THE INVENTION

1. Field of the Invention

The present invention relates generally to transport apparatus for use with an eye drop container, and more particularly to a transport apparatus configured to assist users in increasing their ability to place eye drops in their eyes. The invention is also suitable for medicinal drops such as those frequently used for conditions such as Glaucoma.

2. Description of the Prior Art

In the eyes, the tear film is a complex layer covering the ocular surface. The film lubricates and protects against bacterial invasion and washes out dust and other foreign particles. For millions of people worldwide, however, the natural tears produced by the eyes need to be frequently supplemented for the effective relief of irritated, red, dry, burning, and itching eyes.

Diseases such as Rheumatoid Arthritis, Diabetes, asthma, Thyroid disease, Lupus, and Glaucoma, for example, can further increase eye symptoms. Additionally, a variety of commonly used medications lead to increased dry eye symptoms including antihistamines, blood pressure medications, ulcer medications, diuretics, and antidepressants. Many patients are expected to be on these medications for the rest of their lives and, accordingly, need to regularly utilize eye drops to relieve eye symptoms. Contact lens wearers and patients of laser eye surgery are also particularly susceptible to a variety of eye symptoms requiring the regular use of eye drops. Common activities such as computer use and airplane travel, for example, can also increase the severity of eye symptoms as can extended exposure to air-conditioned and heated environments. It is well known that the body's natural tear volume decreases substantially with age and it is not surprising that a large proportion of regular eye drop users are elderly.

It is imperative that regular users of eye drops have their eye drops conveniently available and easily accessible at all times. In severe cases, a patient may produce a dangerously low quantity or quality of natural tears and will be particularly susceptible to secondary infections. If eye drops are not used at the recommended frequency in such patients, they may eventually develop corneal erosion, scarring and possibly even permanently reduced vision.

Many users of eye drops are concerned about the costs of accidental spillage or leakage of eye drop solution. Due to the high costs of many prescription eye drop solutions, the cumulative costs of solution losses due to accidental spillage and leakage can be substantial. Typical eye drop containers are only completely leak proof when stored in a relatively upright position. In an effort to keep eye drops readily accessible, users have resorted to a wide variety of ways of transporting eye drop containers including putting them in a pocket, purse, briefcase, and the like. Unfortunately, eye drop containers often leak if they are not transported in an upright position. As such, loosely transporting eye drop containers in a pocket, purse, and briefcase, for example, increases the risk of accidental leakage or spillage of the solution.

Proper alignment of an eyeglass container with the eye during application of an eye drop is a difficult task to master and is usually perfected over time with practice. Unfortunately, however, elderly patients and users with poor spatial eye-hand control find it difficult to accurately place eye drops in their eyes. Often, patients seek assistance with this task and have to obtain help from a second person, such as a family member, or nurse, for example. In instances where a second person is unavailable, users may end up wasting several drops of solution before they are finally able to successfully apply the proper dose of eye drops to their eye.

Accordingly, there is an established need for a lightweight, inexpensive, and eye drop container transport apparatus that is capable of retaining an eye drop container in a relatively upright manner and assisting users with increasing their ability to apply eye drops as well as reducing the incidence of spilled, leaked, or otherwise wasted eye drop solution.

SUMMARY OF THE INVENTION

The present invention is directed to a lightweight, inexpensive, and reusable eye drop container transport apparatus that is capable of retaining an eye drop container in a relatively upright manner and assisting users with increasing their ability to apply eye drops as well as reducing the incidence of spilled, leaked, or otherwise wasted solution.

An object of the present invention is to provide an eye drop container transport apparatus that is capable of retaining an eye drop container in a relatively upright manner.

A further object of the present invention is to provide an eye drop container transport apparatus that is capable of assisting users in increasing their ability to apply eye drops to the eye.

Another object of the present invention is to provide an eye drop container transport apparatus that is configured to reduce the incidence of spilled, leaked, or otherwise wasted eye drop solution.

An additional object of the present invention is to provide an eye drop container transport apparatus that is lightweight, reusable, and inexpensive.

In accordance with a first aspect of the invention, an eye drop container anchoring apparatus is provided including a clip portion so that it can be secured to an eye drop container. An elongate support arm extends from the clip portion and helps secure the eye drop container transport apparatus in place. A first and second sight is provided to enable users in increasing their ability to apply eye drops to their eyes while minimizing spillage and wasted solution.

Another object of the present invention is to provide an eye drop container transport apparatus that is capable of removably securing an eye drop container to a wide variety of locations.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION OF THE PREFERRED EMBODIMENTS

Shown throughout the figures, the present invention is generally directed towards a lightweight, inexpensive, and reusable eye drop container transport apparatus that is capable of retaining an eye drop container in a relatively upright and conveniently accessible manner and assisting users with accurately applying eye drops as well as reducing the incidence of spilled, leaked, or otherwise wasted solution.

Figure 1:
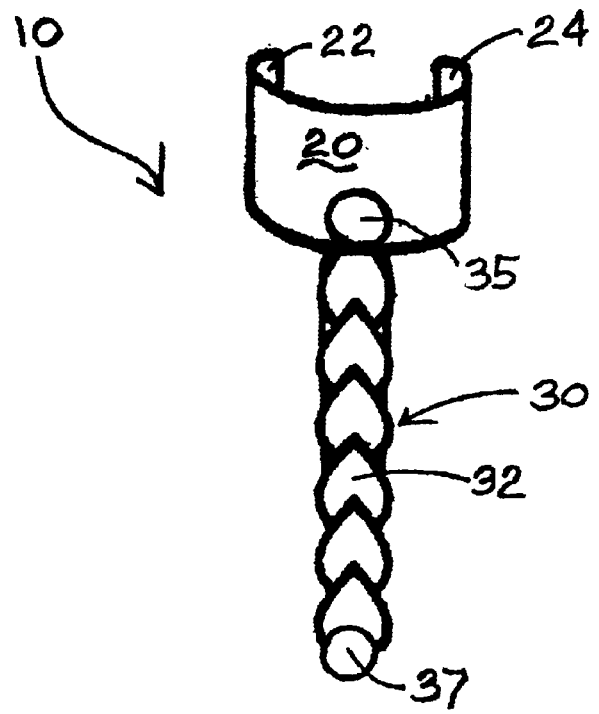
FIG. 1 is a perspective view of a preferred embodiment of the eye drop container transport apparatus of the present invention before it is secured to an eye drop container.
Figure 2:
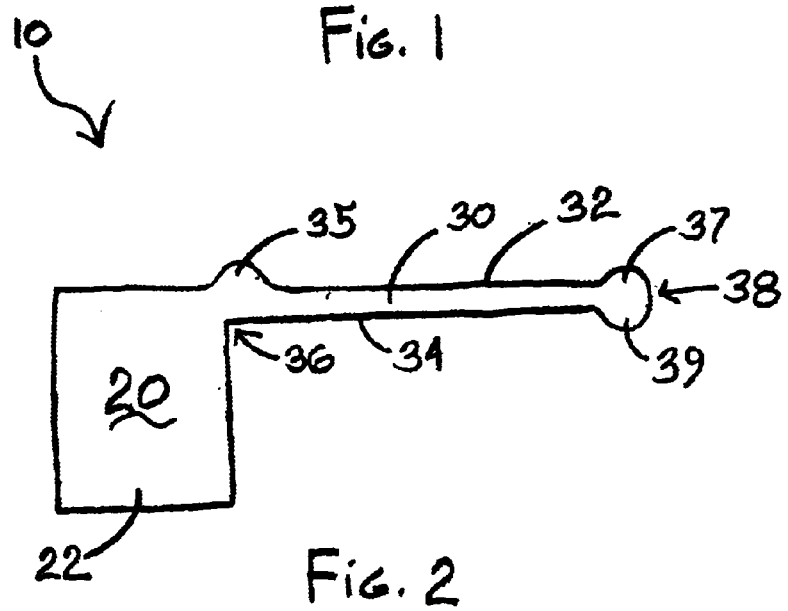
FIG. 2 is a side view of a preferred embodiment of the eye drop container transport apparatus of the present invention before it is secured to an eye drop container.
Figure 3:
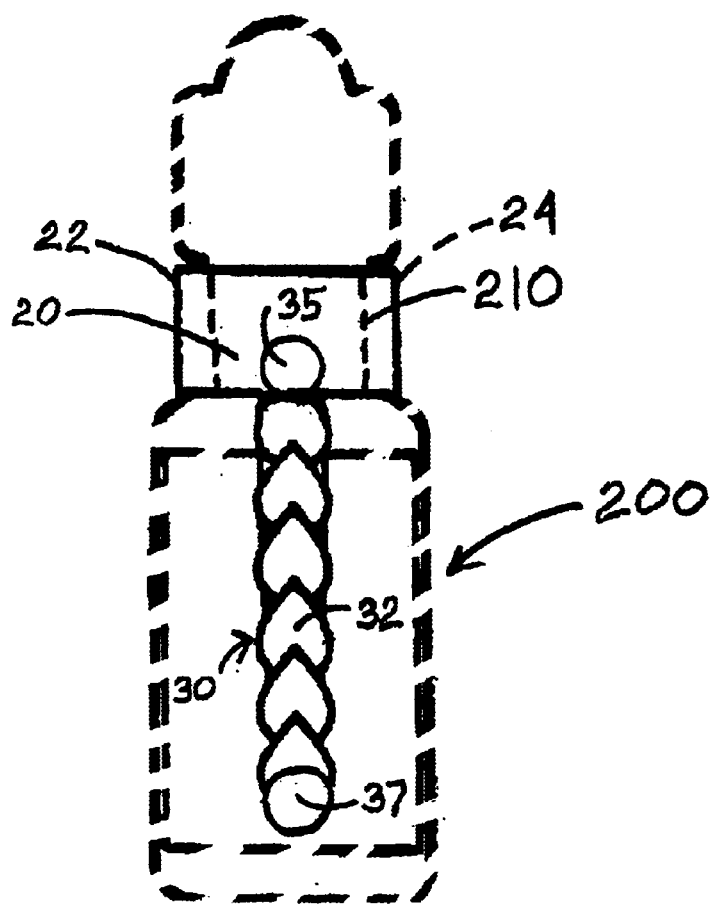
FIG. 3 is a front view of a preferred embodiment of the eye drop container transport apparatus of the present invention after it is secured to an eye drop container in accordance with the present invention.

Referring to FIGS. 1–2, the eye drop container transport apparatus, shown generally as reference numeral 10, is illustrated in accordance with a preferred embodiment of the invention before it is secured to an eye drop container. In FIG. 3, a preferred embodiment of the present invention is shown after it is secured to an eye drop container 200.

As shown in the figures, the eye drop container transport apparatus 10 of the present invention includes a clip portion 20 that is preferably removably secured to the neck 210 of an eye drop container 200 as best shown in FIG. 3. It is seen that the clip portion 20 may be secured to the neck 210 of an eye drop container by a wide variety of known ways without departing from the present invention. In the preferred embodiment, the clip portion 20 is generally "C" shaped and includes a first tang 22 and a second tang 24 as best shown in FIG. 1. As shown in FIG. 3, the first and second tangs 22, 24 substantially surround the neck 210 of the eye drop container 220. It will be appreciated that although typical half-ounce and one ounce eye drop containers 200 are preferred, a wide variety of containers 200 having different sizes, shapes, and volumes may be utilized without departing from the present invention.

The clip portion 20 of the present invention may be constructed out of a wide variety of known materials without departing from the present invention. Preferably, the clip portion 20 will be constructed of a lightweight and inexpensive material such as Aluminum or plastic, for example. An advantage of utilizing a pliable material such as Aluminum is that an inside diameter of the clip portion 20 can easily be adjusted to fit the neck portion 210 of eye drop containers 220 of different sizes and configurations. This can also be accomplished, of course, with known plastics, rubberized materials, some types of nylon, and an array of other known man-made and synthetic materials.

In the preferred embodiment of the eye drop container transport apparatus 10 of the present invention, an elongate support arm 30 extends from the clip portion 20 as best shown in the figures. The elongate support arm 30 of the eye drop container transport apparatus 10 includes an outer surface 32, an inner surface 34, a secured end 36, and a free end 38 as best shown in FIG. 2. As best shown in FIGS. 1 and 3, the outer surface 32 of the elongate support arm 30 of the eye drop container transport apparatus 10 may include decorative insignia such as the eye drop design depicted, for example. The decorative insignia may be constructed using any of a wide variety of known methods including painting, molding, carving, and stamping, for example, and can include any of a number of different designs.

The elongate support arm 30 may be constructed in a wide variety of ways without departing from the present invention. Preferably, the elongate support arm 30 and the clip portion 20 of the eye drop container transport apparatus 10 will be integrally formed as a single piece. Other configurations are possible, of course, such as having the elongate support arm 30 formed as a separate unit and subsequently secured to the clip portion 20 by any of a number of known methods such as by welding or gluing them together, for example.

In the preferred embodiment, the eye drop container transport apparatus 10 will include a first and second sight 35, 37, as shown in the figures, to assist users in accurately applying eye drops while reducing the incidence of spilled, leaked, or otherwise wasted solution. It will be appreciated that many different types of known sights may be used for the purposes of assisting users in accurately applying eye drops. In the preferred embodiment, the first sight 35 will be located near the secured end 36 of the elongate support arm 30. Preferably, the first sight 35 will simply be an engorgement on the outer surface 30 of the elongate support arm 30 as shown. The second sight 37 will preferably be disposed near the free end 38 of the elongate support arm 30. In the most preferred embodiment, the second sight 37 may be formed as a sphere-like engorgement on the free end 38 of the elongate support arm 30 as shown. The portion of the sphere-like engorgement on the outer surface 32 of the elongate support arm 30 comprises the second sight 37 as best shown in FIG. 2. While applying eye drops, a user lifts the eye drop container transport apparatus along with the secured eye drop container and turns it upside down while noting the first and second sight 35, 37. While tilting back their neck, the user then aligns the first sight 35 located near the secured end 36 of the elongate support arm 30 with the second sight 37 located on the free end 38 of the elongate support arm 30. If desired, the user can pull down his or her lower eyelid to form a pocket for excess liquid, and slowly squeeze a drop into the eye. If desired, the user can fixate only on the second sight 37, while applying the eye drops, and ignore the first sight 35.

A retaining anchor 39 will preferably be disposed on the free end 38 of the elongate support arm 30 as shown. Preferably, the retaining anchor 39 will be formed as a sphere-like engorgement on the outer surface 32 of the elongate support arm 30. The portion of the sphere-like engorgement on the inner surface 32 of the elongate support arm 30 comprises the retaining anchor 39 as best shown in FIG. 2.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

I claim:

1. An eye drop container transport apparatus comprising:
   a generally "C" shaped clip portion configured to be removably secured around a neck of an eye drop container,
   an elongate support arm extending from said generally "C" shaped clip portion and having an outer surface, an inner surface, a secured end, and a free end,
   a first sight disposed on said outer surface of said elongate support arm near said free end thereof, a second sight disposed on said outer surface of said elongate support arm near said secured end thereof, said first and second sights comprising engorgements on said outer surface of said elongate support arm, and a retaining anchor disposed on said inner surface of said elongate support arm near said free end thereof.

2. An eye drop container transport apparatus as recited in claim 1 wherein said clip portion is configured to substantially surround said neck of said eye drop container.

3. An eye drop container transport apparatus as recited in claim 1 wherein said clip portion and said elongate support arm are integrally formed.

4. An eye drop container transport apparatus as recited in claim 1 wherein said outer surface of said elongate support arm includes a decorative insignia thereupon.

5. An eye drop container transport apparatus as recited in claim 1 wherein said first and second sights are engorgements on said outer surface of said elongate support arm.

6. An eye drop container transport apparatus as recited in claim 1 wherein said free end of said elongate support arm includes an engorgement thereupon forming said first sight and said retaining anchor.

7. An eye drop container transport apparatus comprising:

a generally "C" shaped clip portion configured to be removably secured to and substantially surround a neck of an eye drop container, an elongate support arm extending from said generally "C" shaped clip portion and having an outer surface, an inner surface, a secured end, and a free end, said outer surface of said elongate support arm including a decorative insignia thereupon, a first sight disposed on said outer surface of said elongate support arm near said free end thereof, a second sight disposed on said outer surface of said elongate support arm near said secured end thereof, said first and second sights comprising engorgements on said outer surface of said elongate support arm, and a retaining anchor disposed on said inner surface of said elongate support arm near said free end thereof.

8. An eye drop container transport apparatus as recited in claim 7 wherein said retaining anchor comprises an engorgement on said inner surface of said elongate support arm.

9. An eye drop container transport apparatus as recited in claim 7 wherein said first and second sights comprise engorgements on said outer surface of said elongate support arm.

10. An eye drop container transport apparatus as recited in claim 7 wherein said clip portion and said elongate support arm are integrally formed.

11. An eye drop container transport apparatus as recited in claim 7 wherein said first and second sights can be utilized by a user to accurately apply eye drops to an eye.

12. An eye drop container transport apparatus as recited in claim 7 wherein said free end of said elongate support arm includes an engorgement thereupon forming said first sight and said retaining anchor.

* * * * *